(12) United States Patent
Nix et al.

(10) Patent No.: US 8,756,071 B2
(45) Date of Patent: Jun. 17, 2014

(54) METHODS AND APPARATUS FOR QUEUE-BASED CLUSTER ANALYSIS

(75) Inventors: Robert Nix, Concord, MA (US); Peter Parnassa, Salem, MA (US); Nikolay Andreev, Waltham, MA (US); William Clayton, Eugene, OR (US); Michael Yun, Kokomo, IN (US); Lauren Fitch, Salem, MA (US); Michael Swain, Newton, MA (US)

(73) Assignee: athenahealth, Inc., Watertown, MA (US)

( * ) Notice: Subject to any disclaimer, the term of this patent is extended or adjusted under 35 U.S.C. 154(b) by 675 days.

(21) Appl. No.: 12/643,453

(22) Filed: Dec. 21, 2009

(65) Prior Publication Data

US 2010/0256985 A1 Oct. 7, 2010

Related U.S. Application Data

(60) Provisional application No. 61/166,351, filed on Apr. 3, 2009.

(51) Int. Cl.
*G06Q 40/00* (2012.01)
*G06Q 10/00* (2012.01)

(52) U.S. Cl.
USPC .................................................. 705/2; 705/3

(58) Field of Classification Search
USPC .......................................................... 705/2
See application file for complete search history.

(56) References Cited

U.S. PATENT DOCUMENTS

| | | | |
|---|---|---|---|
| 5,970,463 A * | 10/1999 | Cave et al. ......................... | 705/3 |
| 7,720,700 B2 * | 5/2010 | Balogh ............................. | 705/4 |
| 7,725,335 B1 | 5/2010 | Goodwin | |
| 7,752,096 B2 | 7/2010 | Santalo et al. | |
| 2004/0073551 A1 | 4/2004 | Hubbard et al. | |
| 2004/0078228 A1 * | 4/2004 | Fitzgerald et al. ............... | 705/2 |
| 2007/0203834 A1 | 8/2007 | Field | |
| 2008/0281632 A1 | 11/2008 | Poley | |

OTHER PUBLICATIONS

Lewellen, et al., "A General Model for Accounts-Receivable Analysis and Control", The Journal of Financial and Quantitative Analysis, vol. 8, No. 2 (Mar. 1973), pp. 195-206.
Stone, "The Payments-Pattern Approach to the Forecasting and Control of Accounts Receivable", Financial Management (1972); Autumn 76, vol. 5 Issue 3, pp. 65-82.
Marakas, "Decision Support Systems in the 21st Century", 1999, Prentice-Hall, Inc., pp. 363-364.

* cited by examiner

*Primary Examiner* — Hiep V Nguyen
(74) *Attorney, Agent, or Firm* — Wolf, Greenfield & Sacks, P.C.

(57) ABSTRACT

Methods and apparatus for identifying and analyzing clusters of medical billing claims in a queue to identify a shared root cause issue for the medical billing claims in the cluster. Exemplary methods and apparatus involve grouping each of the plurality of medical billing claims into clusters based on predetermined cluster patterns that include at least one attribute, validating the clusters using predetermined criteria to determine if the clusters should be analyzed, discarded, and/or marked for further analysis, collecting information about each of the medical billing claims in clusters, and determining a root cause issue for the medical billing claims in the clusters based on the collected information.

30 Claims, 16 Drawing Sheets

FIG. 6

| Cluster Groups | | | | | | | | |
|---|---|---|---|---|---|---|---|---|
| Cluster Pattern | Cluster Name | Score | Score Note | Assigned To | Status | # followup records | # billed records | # worked records |
| BILLINGBATCH | 26423 | 95 | Batch % | | | 0 | 95 | 95 |
| BILLINGBATCH | 26422 | 94 | Batch % | | | 0 | 94 | 94 |
| BILLINGBATCH | 26055 | 88 | Batch % | | | 25 | 0 | 63 | 88 |
| BILLINGBATCH | 26051 | 87 | Batch % | | | 41 | 0 | 35 | 76 |
| BILLINGBATCH | 26417 | 84 | Batch % | | | 0 | 84 | 0 | 84 |
| MEDICALGROUP::IRC | [7]::WC - Workers Comp Other [165] | 48 | Alarm Rate | | | 14 | 5 | 223 | 242 |

FIG. 7

Cluster Group Information

ID: 17C438

Practice:

Pattern: MEDICALGROUP::IRC

Name: [7]:WC - Workers Comp Other [165]

Status:

Assigned To:

Last Researched:

Recommended Kick Code:

Claim Set Description:

Claim Note Text:

Hide Fields Related To

☐ Billing Information  ☐ Claim Age  ☐ Claim Basics  ☑ CSI Details  ☐ Insurance Basics  ☑ Provider Information  ☐ Worked Record Info   [Refresh]

| Insurance Package | Enrollment Category | Service Date | Claim ID | Transfertype | Claim Status | Inflow Date | Outflow Date | Days In Status | Exit FOLLO Kicko |
|---|---|---|---|---|---|---|---|---|---|
| AMERICAN MANUFACTURERS INSURANCE COMPANY [20986] | Workers Comp NY | 11/16/2007 | 521837 | 1 | ATHENAHOLD | 01/28/2009 | 01/30/2009 | 2 | REC |
| AMERICAN MANUFACTURERS INSURANCE COMPANY [20986] | Workers Comp NY | 11/16/2007 | 521837 | 1 | ATHENAHOLD | 02/02/2009 | 02/04/2009 | 2 | RTTI |
| ARROW TRUCKING - WORKERS COMP [46248] | Work Comp | 01/16/2008 | 546614 | 1 | FOLLOWUP | 02/24/2009 | 02/26/2009 | 2 | REC |

FIG. 10

| Insurance Package | Enrollment Category | Service Date | Claim ID | Transfertype | Claim Status | Inflow Date | Outflow Date | Days In Status | Exit FOLLOWUP Kickcode |
|---|---|---|---|---|---|---|---|---|---|
| NEW YORK CITY LAW DEPARTMENT [15563] | Workers Comp NY | 08/07/2008 | 645391 | | BILLED | 02/13/2009 | 02/18/2009 | 2 | W9FORM |
| AMERICAN MANUFACTURERS INSURANCE COMPANY [20986] | Workers Comp NY | 11/16/2007 | 521837 | 1 | ATHENAHOLD | 02/02/2009 | 02/04/2009 | 2 | RTTRVW |
| COOL RISK MANAGMENT [25860] | Workers Comp NY | 07/05/2006 | 695538 | 1 | BILLED | 01/28/2009 | 01/30/2009 | 2 | RTTRVW |
| GCG RISK MANAGEMENT INCORPORATED [16268] | Workers Comp NY | 07/07/2008 | 691482 | 1 | ATHENAHOLD | 02/11/2009 | 02/13/2009 | 2 | RTTRVW |
| NEW YORK CITY LAW DEPARTMENT [15563] | Workers Comp NY | 03/04/2008 | 583266 | 1 | ATHENAHOLD | 02/19/2009 | 02/23/2009 | 2 | RTTRVW |
| NEW YORK CITY LAW DEPARTMENT [15563] | Workers Comp NY | 10/17/2008 | 678091 | 1 | ATHENAHOLD | 02/02/2009 | 02/04/2009 | 2 | RTTRVW |
| NYC TRANSIT AUTHORITY - WORKERS COMPENSATION [15633] | Work Comp | 04/14/2008 | 586339 | 1 | ATHENAHOLD | 02/05/2009 | 02/09/2009 | 2 | RTTRVW |
| NYC TRANSIT AUTHORITY - WORKERS COMPENSATION [15633] | Work Comp | 05/06/2008 | 598356 | 1 | ATHENAHOLD | 02/05/2009 | 02/09/2009 | 2 | RTTRVW |
| COOL RISK MANAGEMENT [25860] | Workers Comp NY | 10/03/2008 | 675673 | 1 | BILLED | 02/02/2009 | 02/04/2009 | 2 | RECALLDROP |
| FRANK GATES CLAIMS [38076] | Workers Comp NY | 08/26/2008 | 652901 | 1 | BILLED | 01/28/2009 | 01/30/2009 | 2 | RECALLDROP |
| MP - PREFERRED MANUFACTURERS INSURANCE TRUST FUND [52169] | Work Comp | 10/16/2008 | 678273 | 1 | BILLED | 01/29/2009 | 02/02/2009 | 2 | RECALLDROP |
| MP - PREFERRED MANUFACTURERS INSURANCE TRUST FUND [52169] | Work Comp | 10/28/2008 | 683909 | 1 | BILLED | 01/29/2009 | 02/02/2009 | 2 | RECALLDROP |
| NEW YORK CITY LAW DEPARTMENT [15563] | Workers Comp NY | 06/03/2008 | 695812 | 1 | BILLED | 02/24/2009 | 02/26/2009 | 2 | RECALLDROP |
| NEW YORK CITY LAW DEPARTMENT [15563] | Workers Comp NY | 07/10/2008 | 629758 | 1 | BILLED | 02/02/2009 | 02/04/2009 | 2 | RECALLDROP |
| NEW YORK CITY LAW DEPARTMENT [15563] | Workers Comp NY | 07/31/2008 | 640597 | 1 | BILLED | 02/02/2009 | 02/04/2009 | 2 | RECALLDROP |
| NEW YORK CITY LAW DEPARTMENT [15563] | Workers Comp NY | 08/07/2008 | 644464 | 1 | BILLED | 02/02/2009 | 02/04/2009 | 2 | RECALLDROP |
| NEW YORK CITY LAW DEPARTMENT [15563] | Workers Comp NY | 08/08/2008 | 645537 | 1 | BILLED | 01/28/2009 | 01/30/2009 | 2 | RECALLDROP |
| NEW YORK CITY LAW DEPARTMENT [15563] | Workers Comp NY | 09/17/2008 | 663378 | 1 | BILLED | 01/28/2009 | 01/30/2009 | 2 | RECALLDROP |
| NEW YORK CITY LAW DEPARTMENT [15563] | Workers Comp NY | 09/17/2008 | 663710 | 1 | BILLED | 02/02/2009 | 02/04/2009 | 2 | RECALLDROP |
| NEW YORK CITY LAW DEPARTMENT [15563] | Workers Comp NY | 09/17/2008 | 666808 | 1 | BILLED | 02/02/2009 | 02/04/2009 | 2 | RECALLDROP |
| NEW YORK CITY LAW DEPARTMENT [15563] | Workers Comp NY | 09/22/2008 | 668311 | 1 | CLOSED | 02/02/2009 | 02/04/2009 | 2 | RECALLDROP |

FIG. 11

| | claimid | transfertype | claimstatus | insurancepackage |
|---|---|---|---|---|
| 1 | 521837 | PRIMARY | ATHENAHOLD | AMERICAN MANUFACTURERS INSURANCE COMPANY [20986] |
| 2 | 383335 | PRIMARY | FOLLOWUP | ARROW TRUCKING - WORKERS COMP [46248] |
| 3 | 546614 | PRIMARY | FOLLOWUP | ARROW TRUCKING - WORKERS COMP [46248] |
| 4 | 577554 | PRIMARY | FOLLOWUP | ARROW TRUCKING - WORKERS COMP [46248] |
| 5 | 594989 | PRIMARY | FOLLOWUP | ARROW TRUCKING - WORKERS COMP [46248] |
| 6 | 645475 | PRIMARY | FOLLOWUP | ARROW TRUCKING - WORKERS COMP [46248] |
| 7 | 690835 | PRIMARY | BILLED | BUNCH & ASSOCIATES [78222] |
| 8 | 666561 | PRIMARY | BILLED | CAMBRIDGE INTERGRATED SERVICES [26005] |
| 9 | 695538 | PRIMARY | BILLED | COOL RISK MANAGMENT [25860] |
| 10 | 675673 | PRIMARY | BILLED | COOL RISK MANAGMENT [25860] |
| 11 | 532258 | PRIMARY | BILLED | ESIS [37814] |
| 12 | 546125 | PRIMARY | BILLED | ESIS [37814] |

Matching Claims in BILLED Status for cluster group 17

Claim Billed Date Range: 02/17/2009 to 03/19/2009

Max Claim Alarm Date: 03/29/2009

Increase maximum output size to 5000 claims. ☐
(Default is 500)

Show claims

| | Claim Alarm | Service Date | Supervising Provider | Department | Transfertype | Kick Code | Billing Batch ID | Batch Format | Insurance Package |
|---|---|---|---|---|---|---|---|---|---|
| 1 | 03/17/2009 | 10/20/2008 | ▬▬▬ | ▬▬▬ | 1 | CHKCUT | | | SEDGEWICK CMS [74737 |
| 2 | 03/27/2009 | 10/21/2008 | ▬▬▬ | ▬▬▬ | 1 | FAXTRACK | | | STATE OF NEW YORK WORKERS COMPENSATION BOARD [48266 |

FIG. 14

Update of the Group

ID Pattern Name                    Cluster Group Name
17  MEDICALGROUP::IRC              [7]:WC - Workers Comp Other [165]

Claim Set Information

Status: UNASSIGNED

Assigned To:

Last Researched: 03/19/2009

Recommended Athena Kickcode: CIP

NOTE: There are no specific kickreason categories applicable to these claims; you will only be able to apply athena kick codes to these claims.

Claimset Description
(limit: 4000 characters): Claims are in Process

Claimnote Text
(limit: 4000 characters): The claims are in still in process with the payer.

Force drop to paper?: No Change

Force drop reason:

Claimset Report Recipient(s): _____@athenahealth.com note: you can send the report to multiple users by providing a comma-separated list of usernames

FIG. 15

Cluster Group Information

| Field | Value |
|---|---|
| ID | 17C438 |
| Practice | |
| Pattern | MEDICALGROUP::IRC |
| Name | [7]::WC - Workers Comp Other [165] |
| Status | UNASSIGNED |
| Assigned To | |
| Last Researched | 03/19/2009 |
| Recommended Kick Code | CIP |
| Claim Set Description | Claims are in Process |
| Claim Note Text | The claims are in still in process with the payer. |

Hide Fields Related To

☐ Billing Information  ☐ Claim Age  ☐ Claim Basics  ☑ CSI Details  ☐ Insurance Basics  ☐ Provider Information  ☑ Worked Record Info    Refresh

| Insurance Package | Enrollment Category | Service Date | Claim ID | Claim Transfertype | Claim Status | Supervising Provider | Department | |
|---|---|---|---|---|---|---|---|---|
| ARROW TRUCKING - WORKERS COMP [46248] | Work Comp | 01/16/2008 | 546614 | 1 | BILLED | ▓▓▓ | ▓▓▓ | 02/27 |
| ARROW TRUCKING - WORKERS COMP [46248] | Work Comp | 03/26/2008 | 577554 | 1 | BILLED | ▓▓▓ | ▓▓▓ | 02/27 |
| ARROW TRUCKING - WORKERS COMP [46248] | Work Comp | 04/30/2008 | 594989 | 1 | BILLED | ▓▓▓ | ▓▓▓ | 02/27 |

FIG. 16

METHODS AND APPARATUS FOR QUEUE-BASED CLUSTER ANALYSIS

RELATED APPLICATIONS

This application claims priority under 35 U.S.C. §119(e) to U.S. Provisional Application Ser. No. 61/166,351, entitled "METHODS AND APPARATUS FOR QUEUE-BASED CLUSTER ANALYSIS," filed on Apr. 3, 2009, which is herein incorporated by reference in its entirety.

TECHNICAL FIELD

The present invention relates generally to the processing of entries in a queue, and more specifically relates to identifying a cluster of entries in the queue in order to process the entries in the cluster at the same time.

BACKGROUND

Lists of records or queues are commonly used to collect and analyze data for a variety of applications. For example, queues may be used to store and track the status of claims issued by a medical services provider. A typical medical services provider, or a third-party acting on behalf of the medical services provider, processes a large volume of claims detailing expenses incurred by patients treated by the medical services provider. Each of these claims includes information and costs associated with one or more procedures or services provided to the patient, and which the medical services provider would like to recover payment. For many patients, payment is recovered by transmitting the claims to the patient's insurance provider or other payer who, in turn, evaluates the charges on the claim and remits the appropriate payment to the medical services provider. Ensuring that this payment process operates smoothly is important to the medical services provider to facilitate payment for the medical services provider's services in a timely manner.

Medical services providers process hundreds or thousands of claims a day. One way to facilitate tracking the status of these claims is to enter the claims as entries in a database which keeps track of, among other things, when the claims were sent and when remittance was received. Due to the large volume of claims being processed, a medical services provider may not receive a response for some claims even though the claims were submitted several weeks or months prior. For each claim in which a response was not received, a follow-up call is typically placed to the payer in order to determine why there was no response. If even a relatively small percentage of the claims do not receive a response, the number of follow-up calls required may be quite large, resulting in a process that is both time-consuming and costly for the medical services provider.

SUMMARY

Some embodiments of the invention are directed to a method of processing a plurality of medical billing claims stored in a queue by defining at least one cluster comprising a subset of the plurality of medical billing claims. The method comprises acts of grouping, using at least one processor, each of the plurality of medical billing claims into the at least one cluster based on at least one predetermined cluster pattern that includes at least one attribute, validating the at least one cluster using predetermined criteria to determine if the at least one cluster should be analyzed or discarded, collecting information, based on the at least one predetermined cluster pattern, about each of the medical billing claims in the at least one cluster, and determining a root cause issue for the plurality of medical billing claims in the at least one cluster based on the collected information.

Some embodiments of the invention are directed to a computer-readable medium encoded with a plurality of instructions, that when executed by a computer, perform method of processing a plurality of medical billing claims stored in a queue by defining at least one cluster comprising a subset of the plurality of medical billing claims. The method comprises acts of grouping each of the plurality of medical billing claims into the at least one cluster based on at least one predetermined cluster pattern that includes at least one attribute, validating the at least one cluster using predetermined criteria to determine if the at least one cluster should be analyzed or discarded, collecting information, based on the at least one predetermined cluster pattern, about each of the medical billing claims in the at least one cluster, and determining a root cause issue for the medical billing claims in the at least one cluster based on the collected information.

Some embodiments of the invention are directed to a medical billing claim processing system comprising at least one processor. The at least one processor is configured to group a plurality of medical billing claims into at least one cluster based on at least one predetermined cluster pattern that includes at least one attribute, validate the at least one cluster using predetermined criteria to determine if the at least one cluster should be analyzed or discarded, collect information, based on the at least one predetermined cluster pattern, about each of the medical billing claims in the at least one cluster, and determine a root cause issue for the plurality of medical billing claims in the at least one cluster based on the collected information.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

The accompanying drawings are not intended to be drawn to scale. In the drawings, each identical or nearly identical component that is illustrated in various figures is represented by a like reference character. For purposes of clarity, not every component may be labeled in every drawing. In the drawings:

FIG. 6 is a display of a user interface produced by a portion of a software program used to analyze clusters generated in accordance with some embodiments of the invention;

FIG. 7 is a display of a cluster report produced by a portion of a software program used to analyze clusters generated in accordance with some embodiments of the invention;

FIG. 10 is a display of individual claim information produced by a portion of a software program used to analyze clusters generated in accordance with some embodiments of the invention;

FIG. 11 is a display of detailed claim information produced by a portion of a software program used to analyze clusters generated in accordance with some embodiments of the invention;

FIG. 12 is a display of a claim processing interface produced by a portion of a software program used to analyze clusters generated in accordance with some embodiments of the invention;

FIGS. 13A and 13B are respectively a display of a user interface for entering notes and a display of a user interface for editing claim information, both of which are produced by portions of a software program used to analyze clusters generated in accordance with some embodiments of the invention;

FIG. 14 is a display of a user interface for detecting claims outside of a worked cluster, the user interface being produced by a portion of a software program used to analyze clusters generated in accordance with some embodiments of the invention;

FIG. 15 is a display of an administrative user interface produced by a portion of a software program used to analyze clusters generated in accordance with some embodiments of the invention; and FIG. 16 is a display of a report generating interface produced by a portion of a software program used to analyze clusters generated in accordance with some embodiments of the invention.

DETAILED DESCRIPTION

The present disclosure generally relates to inventive methods and apparatus for processing entries in a queue, and more specifically to identifying and analyzing clusters of entries in the queue that share common features. A typical medical billing practice processes hundreds or thousands of claims a day by transmitting the claims to a payer such as an insurance company or clearinghouse. The payer usually returns a remittance or denial. However, a certain percentage of the submitted claims do not receive a response from the payer and follow-up, called "claim tracking," is performed to ensure that the corresponding medical services provider receives proper payment for their services. The status of all submitted claims may be tracked by including information about the claims as entries in an electronic queue such as a database, or in any other suitable electronic format. For each claim that has not received a response after a predetermined amount of time, a follow-up communication to the payer may be initiated to determine the source of the non-response. As the volume of claims processed by a medical billing practice increases, the number of follow-up communications and the length of time before the medical services provider is paid increases.

Applicants have recognized and appreciated that multiple entries in a queue may share common features, and that by grouping the multiple entries together into a cluster, the multiple entries in the cluster may be processed in parallel. For example, if the queue comprises claims for which a response has not been received from a payer, a common root cause relating to why the response has not been received may underlie several of the claims in the queue. Identifying clusters in a queue which may share a common root cause, and addressing the common root cause may obviate the need to follow-up on each of the claims in the queue separately resulting in an efficient problem resolution process.

Figure 1:
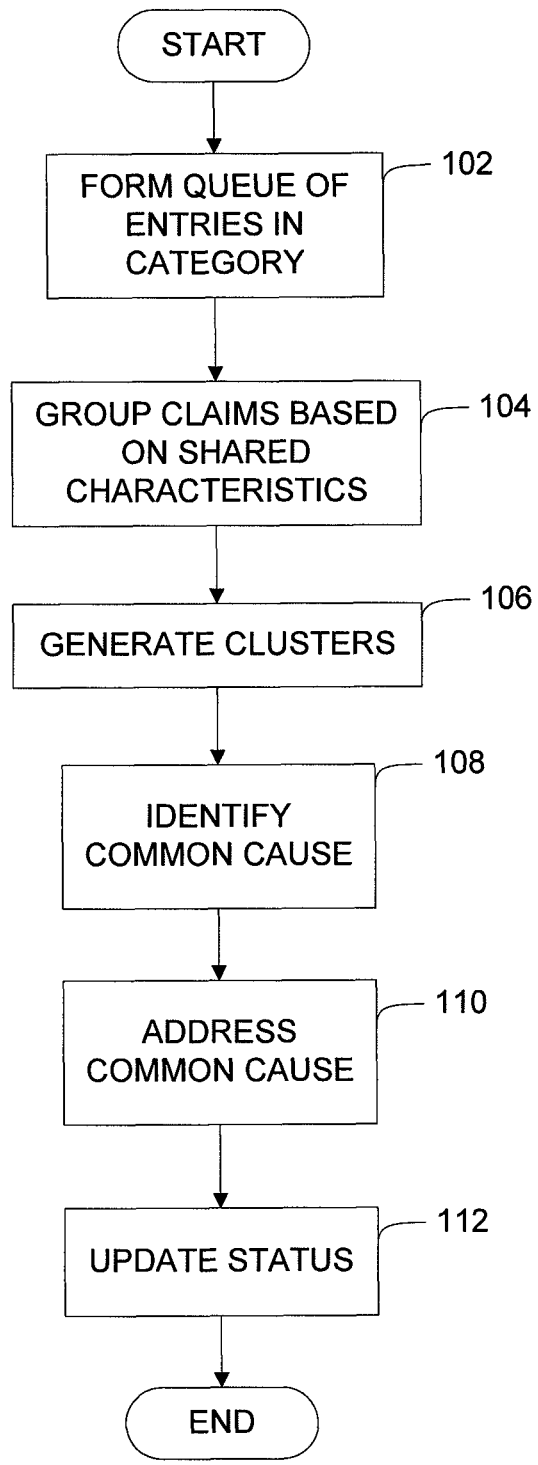
FIG. 1 is a flow chart queue-based cluster analysis process according to some embodiments of the invention.

To this end, some embodiments of the invention are directed to methods and apparatus for identifying candidate clusters of entries (e.g., claims which have not received a response) in a queue that share at least one common feature, and analyzing the candidate clusters to determine a common underlying cause (e.g., why a response has not been received for the claims in the cluster). An exemplary illustration of a method for processing claims in a queue is provided in FIG. 1. In act 102, claims belonging to a particular category are collected into a queue. For example, each claim that is submitted to a payer may have an estimated time window within which a response is typically received. When a response is not received within this time window, the status of the claim may be changed (e.g., to "Followup") to indicate that a follow-up communication should commence. The status of a claim may be stored as part of the entry for the claim in a queue or in any other suitable way, such as metadata associated with the entry for the claim. All claims in which the status was changed to "Followup" over the course of a predetermined time frame may be collected into a queue in act 102 in order to be processed. For example, all claims marked as "Followup" within the last sixty days may be collected into a queue for further analysis. It should be appreciated that a particular category used to form the queue in act 102 is not limited to claims without a payer response, but the particular category may alternatively be related to denied claims, claims on hold, or any other issue which would benefit from further investigation to determine a common root cause.

After forming a queue of claims in act 102, the claims in the queue are grouped based on shared characteristics in act 104, as described below in more detail. Although some claims may be included in only a single group, other claims may be included in more than one group provided that the claims have shared characteristics with claims in multiple groups. Groups of claims that meet certain criteria are classified as clusters in act 106. In some embodiments, groups may need to comprise a minimum number of claims to be considered a cluster. In addition to a minimum number of claims, other exemplary criteria may also be used when generating clusters and embodiments of the invention are not limited in this respect.

Clusters generated in act 106 are analyzed in act 108 to identify at least one common root cause why the claims have been included in the particular category that is being investigated (e.g., submitted claims without a response). Exemplary ways of analyzing clusters according to some embodiments of the invention are described in more detail below.

After a common root cause has been identified for claims in a cluster, the root cause is addressed to remedy the problem. For example, the common root cause identified in act 108 may be an incorrect pay-to address. In this example, the pay-to address may be corrected in act 110, and the claims in the cluster may be resubmitted to the payer with the corrected pay-to address. It should be appreciated that the common root cause may be addressed by a user with or without directed guidance, or the process may be automated. For example, in some embodiments, options of how to address a root cause issue may be presented to a user and the user may choose from among the options. The options may be presented as a decision tree on a user interface, or in any other suitable way. A further description of a directed cluster group resolution for use with some embodiments is provided below. In other embodiments, software executed on a computer may be used to automatically select an option for addressing the root cause issue without user intervention.

The status of the claims in a cluster that has been analyzed or "worked" is updated in act 112. For example, the status of the claims in a processed cluster may be changed from "Followup" to some other status to indicate that follow-up has been performed on all of the claims in the cluster. Thus, only a limited number of follow-up communications are necessary to process all of the claims in a cluster due to their shared common root cause.

In some embodiments, information about a resolution process for the root cause of a cluster is recorded so future claims having similar attributes may be processed in the same way as the claims in the cluster. The resolution process may be recorded by storing a cluster pattern and the root cause identified for the claims in a cluster for a predetermined amount of time (e.g., one year). By storing this information, new claims that arise during the predetermined amount of time are processed similarly to the claims in the cluster, but new claims that arise outside of this time window are handled differently. It should be appreciated that information about a resolution process may be stored in any suitable manner and for any desired length of time and embodiments of the invention are not limited in this respect.

As discussed above, in some embodiments, a user may be guided through a cluster resolution process based on stored information from at least one prior cluster resolution process. For example, the information may be stored in one or more "weighted" decision trees that can be used to generate directed guidance for cluster resolution. In one embodiment, a user may be guided based on the type of cluster, as well as other data that is currently available. For example, if a user is working on a cluster that has the type "billing batch," a user interface may prompt the user with the question, "Have any claims from this billing batch been paid?" It should be appreciated that the prompt may be presented to the user in any form including, but not limited to, visually presented on a computer screen or auditorily presented via a speaker or headphones. Depending on the response provided by the user, a user may be prompted with a different question to help guide the user through the cluster resolution process. For example, if the user indicates that at least some of the claims have been paid, the user may be prompted with one or more questions to investigate the breakdown of payments by provider.

In some embodiments employing directed cluster resolution, the directed cluster resolution process may be partially or fully automated in which one or more prompts generated by querying a decision tree are automatically responded to based on stored information about the most likely responses to each prompt. During or following automated directed cluster resolution, a user may be presented with findings and/or recommendations regarding additional follow-up for the cluster resolution. For example, upon selecting an "investigate" link, a user may be presented with a summary of the data generated by the directed cluster resolution process. Together with the summary of the data, one or more additional prompts may be presented to a user who may, in turn, supply a response to continue the automated directed cluster resolution process.

Some embodiments employing automated directed cluster resolution may automatically gather information based on prompts generated during a cluster resolution process. For example, if it is determined during automated directed cluster resolution, that particular information is needed to continue the cluster resolution process, one or more prompts may automatically be sent to users who may be specifically able to respond to the prompt by providing the particular information. Automated information gathering may also be integrated with one or more of the cluster identification and/or resolution processes described in more detail below, each of which may be implemented as a manual process, a partially automated process, or a fully automated process, with or without directed guidance.

Some embodiments are directed to methods and apparatus for claim tracking, in which claims that do not receive a timely response from a payer are identified, and for each claim that is identified, information that may be useful in determining a common cause is collected. Table 1 illustrates exemplary information that may be collected for each claim that is identified, although other information may also be collected and embodiments of the invention are not limited in this respect.

In some embodiments, determining when a claim should be included in a queue for clustering analysis may be performed by setting an alarm date for each claim that is submitted to a payer. If a response is not received from the payer by the alarm date, the alarm is triggered and the status of the claim is changed to Followup. Alternatively, an alarm may be deactivated if a response is received prior to the alarm date. Alarm dates may be determined based on a number of factors including, but not limited to, historical performance data for a payer, the complexity of the claim, the time of year when the claim is submitted, or any other factors which are related to a billing cycle. Although setting alarms is one example of a process for ensuring that claims are properly tracked, other methods may be used, and embodiments of the invention are not limited in this respect. For example, in some embodiments, other claims (for example, in Billed status) that do not receive a response from a payer within a fixed amount of time, regardless of the payer's identity, may be used in the cluster analysis described above.

After information has been collected on at least some of the claims in the queue to be analyzed, cluster identification methods may be used to identify candidate clusters of claims that might be being processed incorrectly due to a shared root cause or problem.

TABLE 1

Exemplary Information Collected for Claims

Practice
Provider
Medical Group
Department
Insurance Package
Insurance Reporting Category
Enrollment Category
Claim Submission Category
Billed Date
Billing Batch
Batch Format
EMC Receiver
Date of Response (including Follow-up calls)
Follow-up Call Result Code (if available)
Claim Status Inquiry (CSI) Result Code (if available)

Figure 2:
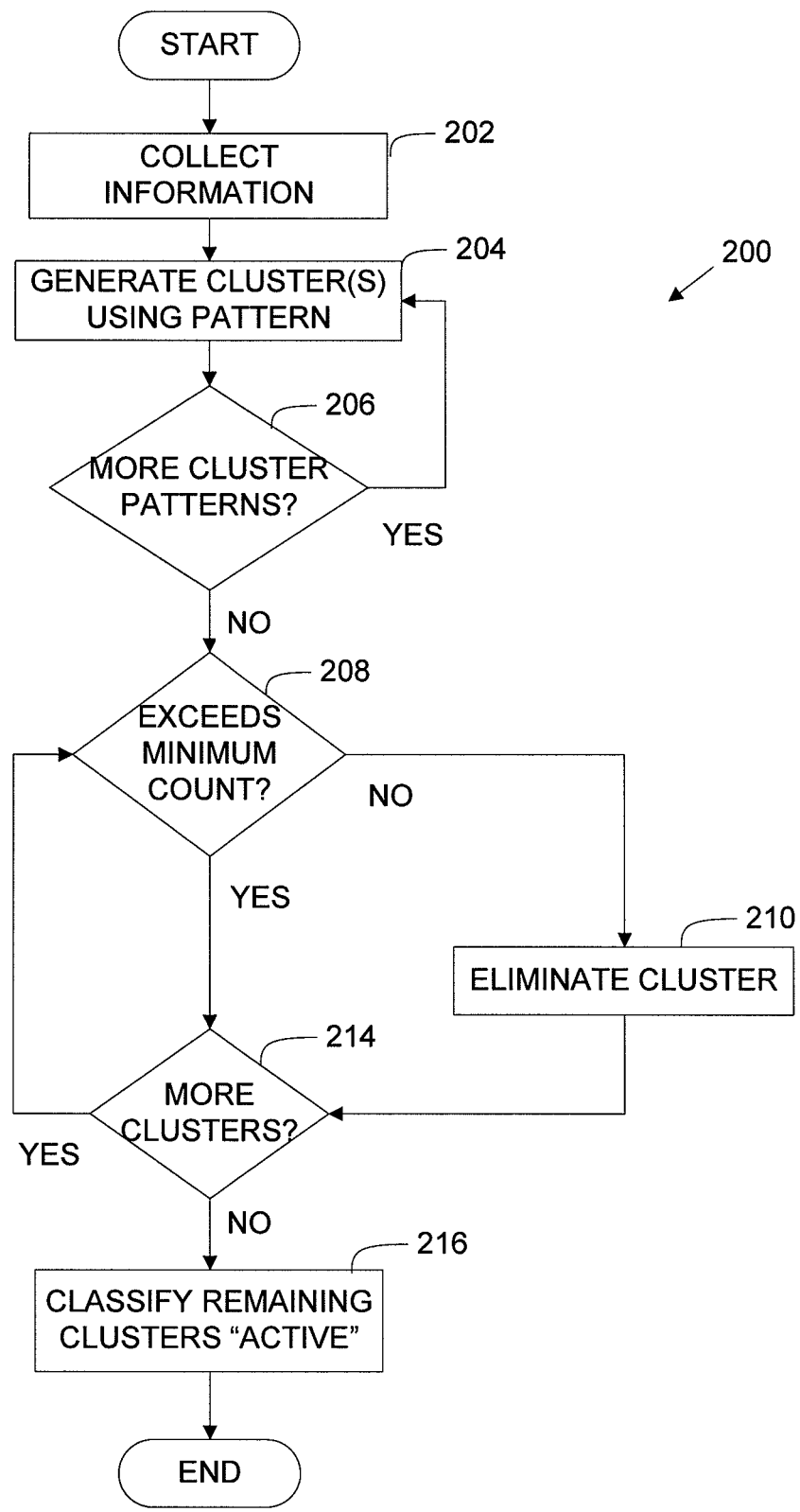
FIG. 2 is a flow chart of a cluster identification process according to some embodiments of the invention.

A cluster identification process 200 in accordance with some embodiments of the invention is illustrated in FIG. 2. For the purposes of illustration, the cluster identification process 200 will be applied to the example provided above in which claims that have triggered an alarm due to the lack of a response from a payer are analyzed. However, it should be appreciated that the cluster identification process 200 may also be used to identify other types of clusters (e.g., denial claim clusters), and embodiments of the invention are not limited in this respect. The cluster identification process 200 is driven by a configurable set of "cluster patterns" that define a set of attributes that claims would have in common if the delay in payer response was due to the same root cause.

As described above, and illustrated as act 202, detailed information is collected for each claim in the queue used for cluster identification. This detailed information may be related to the attributes shown in Table 1 or any other suitable attributes that would assist in categorizing claims into clusters based on a common underlying cause. In some embodiments, detailed information may be stored in a denormalized table in a relational database, although the information may be stored in any other suitable form and embodiments of the invention are not limited in this respect.

After collecting the detailed information for each claim in act 202, the claims are grouped together along dimensions outlined by a set of predefined cluster patterns. The cluster patterns are indicative of a common root cause or problem. Exemplary cluster patterns, to which the embodiments of the invention are not limited, are shown in Table 2. Although only six cluster patterns are illustrated in Table 2, it should be appreciated that any attributes (including those in Table 1 or otherwise) may be combined to define cluster patterns and embodiments of the invention are not limited in this respect.

TABLE 2

Exemplary Cluster Patterns

Billing Batch
Insurance Reporting Category:: CSI Result Type
Medical Group:: Batch Format:: Insurance Package
Medical Group:: Batch Format:: Insurance Reporting Category (IRC)
Medical Group:: Claim Submission Category
Medical Group:: Insurance Reporting Category For each defined cluster pattern, clusters are generated in act 204 based on the claims included in the queue. As described above, a claim may be included in the queue based on numerous criteria including, but not limited to, the claim's current status or if the status of the claim is anticipated to change in the near future. For example, in some embodiments, claims that have been changed to Followup status in the past sixty days may be included in the queue along with claims that are close to their alarm date. By also including claims that are close to their alarm date, these claims are dealt with proactively, rather than waiting until an alarm has been triggered.

In some embodiments, claims in the queue are grouped using the defined cluster patterns in a sequential manner. With reference to Table 2, which defines six cluster patterns, claims may first be grouped according to the attribute "Billing Batch," and clusters based on this pattern are generated in act 204. After claims are grouped according to the attribute "Billing Batch," it is determined in act 206 if there are other defined cluster patterns to be analyzed. If there are other defined cluster patterns, another cluster pattern is selected and claims are grouped according to the shared attributes in the new cluster pattern. For example, continuing the example above, claims may be grouped according to the next defined cluster pattern (e.g., Insurance Reporting Category::CSI Result in Table 2) and clusters may be generated based on these shared attributes. In some embodiments, the process continues until all defined cluster patterns have been analyzed, although in other embodiments only a subset of defined cluster patterns may be analyzed. If it is determined in act 206 that no other cluster patterns are to be analyzed, each of the clusters is screened according to predefined criteria to determine if the cluster should be analyzed or discarded.

Applicants have appreciated that it may be useful to only analyze clusters having a minimum number of claims (e.g., 100 claims), or at least to address clusters having a large number of claims first. Thus, in some embodiments, it is determined in act 208 if the number of claims in each cluster exceeds a predetermined threshold value. If the number of claims in the cluster does not exceed the threshold value, the cluster is eliminated in act 210 and it is determined in act 214 if there are more clusters to be screened. If it is determined in act 214 that there are more clusters to be screened, another cluster is selected and it is determined in act 208 if the number of claims in this cluster exceeds the threshold value.

An illustrative example of the above-described thresholding process is as follows: Cluster A generated based on the "Medical Group::Claim Submission Category" cluster pattern has 500 claims. The value of the attribute Medical Group is "ABC Medical Group" and the value of the attribute Claim Submission Category is "123 Submissions." Cluster B generated based on the same cluster pattern has 5 claims, and has values of Medical Group="DEF Medical Group" and Claim Submission Category="456 Submissions." If the threshold was set at 100 claims, cluster A would survive, but cluster B would be eliminated in act 210 because the number of claims in cluster B is too small to justify investigation through cluster analysis.

Other screening steps in addition to cluster size analysis may be included and embodiments of the invention are not limited in this respect. In some embodiments, clusters may be screened based on whether a pattern characteristic (i.e., cluster pattern and values) is too general to result from a single root cause. For example, a cluster generated based on the cluster pattern "Medical Group::Insurance Reporting Category" that refers to the "Legal" IRC may be eliminated because the "Legal" IRC refers to too wide a variety of insurance companies, and it is likely that the claims in the cluster do not share the same root cause.

In some embodiments, when a potentially new cluster is identified, it may first be determined whether the potentially new cluster already exists in a database used to store the generated clusters. Determining if the potentially new cluster already exists reduces the possibility of duplicate clusters which may unnecessarily cause the same cluster to be worked multiple times.

In some embodiments, elimination of a cluster in act 210 results in the status of the claims in the cluster remaining unchanged (e.g., the claims in the cluster remain in Followup status), although in other embodiments, clusters that are eliminated may form a claim tracking queue in which each claim in the claim tracking queue is addressed by a follow-up communication in a one-by-one manner.

In some embodiments, claims may be segmented into tiers based on various characteristics, and different groups of users may be responsible for working claims in each tier. For example, claims that are eliminated from the cluster identification process and are placed in a claim tracking queue, may transition from one tier (e.g., the cluster ID tier) to a different tier (e.g., the claim tracking tier) so that ownership of the claims between the two groups is clearly indicated. It should be appreciated that any suitable communication mechanism may be used to communicate the ownership of claims worked by different groups of users, and the aforementioned description of a tier-based system is only one possible implementation.

Once it is determined that all of the clusters have been screened, the remaining clusters are classified as "Active" in act 216 and information about the cluster is added to a cluster database that, among other things, may be used to analyze future claims having similar attributes as described above.

Some embodiments are directed to methods and apparatus for processing of denial claims. Unlike claim tracking, where no response has been received in response to submitting a claim to a payer, a denial refers to a claim that was either submitted to a payer and was at least partially rejected for payment, or a claim that was identified as likely to be denied, if submitted to a payer. Medical services providers often appeal claims that were submitted to a payer and which received a rejection (or partial rejection) decision. Applicants have recognized that since the appeal process is often complex, a cluster resolution process that groups denials with similar characteristics for submission to a payer as a mass appeal (e.g., compared to submitting an appeal for each claim), may improve the efficiency of the appeal process. Additionally, by grouping denials into clusters, information about a root cause identified for the rejections of the claims in a denial cluster may be provided to a provider, in order to prevent rejections of claims submitted to payers in the future. Furthermore, one or more processing rules may be created based on the denial clusters to prevent some claims from being sent to a payer until the likely denial is resolved.

Various cluster patterns may be defined to identify and analyze denial clusters. A non-exhaustive list of cluster patterns for identifying and/or analyzing denial clusters includes: Billing Batch ID, Insurance Reporting Category:: Kickcode, Created By, Insurance Reporting Category::Previous Denial, and Claim Rule ID. Denial clusters may comprise claims denied as a result of feedback from a payer and/or claims identified as likely to be denied should the claims be submitted to a payer.

In some embodiments, the identification of a denial cluster begins by collecting denied (or likely to be denied) claims received over a predetermined time window (e.g., 60 days). For each denied claim, standard information, such as the insurance package and the supervising provider, and other information that may help with classifying the denied claim (e.g., the procedure code(s) listed on the claim), may be collected. Denial clusters are then formed based on the one or more predefined cluster patterns using a cluster identification process, such as cluster identification process 200 described above.

Applicants have identified that the analysis of denial clusters includes at least two characteristics which distinguish their processing from the claim tracking cluster processing described above. For example, claims are often denied for multiple reasons at the same time. For this reason, it may be determined whether denied claims were part of a group of denials, and if so, the resolution of these denied claims may occur in multiple stages. One example of this type of scenario is when a provider issue should be corrected before a procedure code issue can be resolved. Additionally, in some cases, information from a previous denial may be of more interest than information included with a denial currently being processed. For example, a provider may indicate that there was a problem with a particular claim. However, in some embodiments, information from one or more previous denials on the same claim may be considered more relevant in classifying the particular claim than a more recent denial on the claim itself.

Identification and processing of denial clusters, due to their complexity, may require additional analyses than the analyses described above for cluster identification for claim tracking purposes. That is, resolving denial clusters may involve facilitating issues regarding items such as: combinations of procedure codes on a claim, combinations of procedures codes and diagnosis codes, differences in adjudication policy between a primary and a secondary payer, and/or interpreting combinations of denials on a single claim.

It should be appreciated that denial clusters may be processed using different data structures than those used for clusters in claim tracking. For example, in some embodiments, it may be possible to investigate subsets of groupings (e.g., subsets of procedure codes on a claim) and/or using a cross-dimensional "market-basket" analysis (e.g., which procedure code/diagnosis code groupings lead to the most denials).

In some embodiments, a relational database is used to store clusters and information about the clusters. Clusters may be stored as records in a clusterrecord table, and general information about the clusters may be entered as a single record in a clustergroup table. For example, the clustergroup table may include information such as the identifier and name of the cluster and whether it is "active cluster" or a "duplicate cluster." As used herein, the term "duplicate cluster" is used to refer to a cluster which shares a predetermined percentage of claims with another cluster. Detailed information regarding component "key-value" pairs that define the cluster may be stored in a clustergroupvalue table. For example, the clustergroupvalue table may include information stating that the claims in the cluster have a Medical Group ID of 1 and a Claim Submission Category ID of 10. After storing a cluster in the relational database, claims embodied as cluster records in the relational database may be associated with the cluster.

As described above, some claims can belong to more than one cluster. For example, a claim can belong to one cluster generated based on the "Billing Batch" cluster pattern and another cluster generated based on the "Medical Group:: Claim Submission Category" cluster pattern. To facilitate querying against clusters generated based on different cluster patterns, in some embodiments in which a relational database is employed, a bridge table may be created, which includes a record that lists the cluster record ID along with the ID of the cluster to which it belongs.

Applicants have recognized that some clusters may have a substantial amount of shared claims between them. Accordingly, in some embodiments, stored clusters may be reviewed for duplicates. Some clusters may be flagged as duplicates if they share a predetermined percentage of claims. In some instances, duplicate clusters may be identical, although in other instances duplicate clusters may only share a majority of their claims. Determining whether clusters are duplicates may be performed in any suitable way and embodiments of the invention are not limited in this respect.

After the clusters have been added to the database, in some embodiments, the clusters are scored to determine a likelihood that the claims share a root cause issue. One or more algorithms, described in more detail below, may be used to determine the score for a cluster.

Applicants have recognized that cluster identification techniques according to embodiments of the present invention may also be useful in systems that assist multiple providers to receive payment from multiple payers. Such an system may be used, for example, by a third party who assists medical services providers in collecting payments for claims by submitting the claims to insurance companies or other payers on behalf of the medical services providers. The third party may use information that is gathered across multiple providers and payers to address common root cause issues that may arise in such systems.

Figure 3:
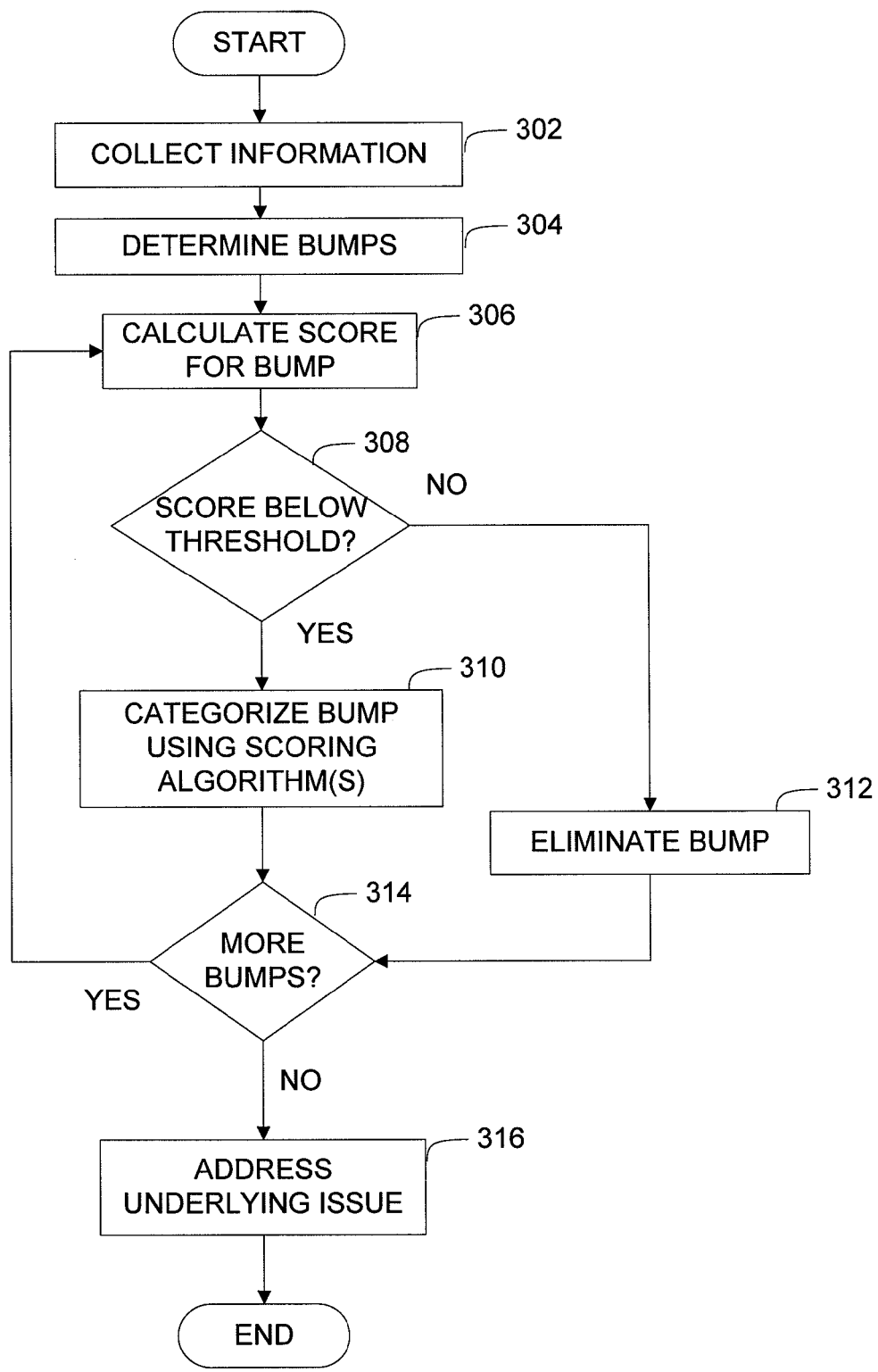
FIG. 3 is a flow chart of a Naïve Bump Hunting process for use with some embodiments of the invention.

To this end, another type of cluster identification analysis 300, for use with some embodiments of the invention is called "Naïve Bump Hunting" and is illustrated in FIG. 3. In this approach, anomalies in a payer billing cycle are detected and categorized by comparing actual returns to expected returns. In Naïve Bump Hunting, the survival distribution of claims at a particular payer across multiple providers is determined. Applicants have recognized that in systems with a large sample size (i.e., many providers), survival distributions can be estimated empirically across many dimensions including, but not limited to, medical group, individual provider, payer, claim format, and expected remittance format. For each of these dimensions, the empirical survival distributions may be compared to the actual survival distribution for a particular dimension set, and positive deviations or "bumps" (actual greater than empirical) are identified and analyzed.

A first step in Nave Bump Hunting, in accordance with some embodiments of the invention, is to collect information about claims to be analyzed in act 302. At least some of the information that may be collected in act 302 is illustrated in Table 3.

TABLE 3

Exemplary Claim Information

Figure 4A:
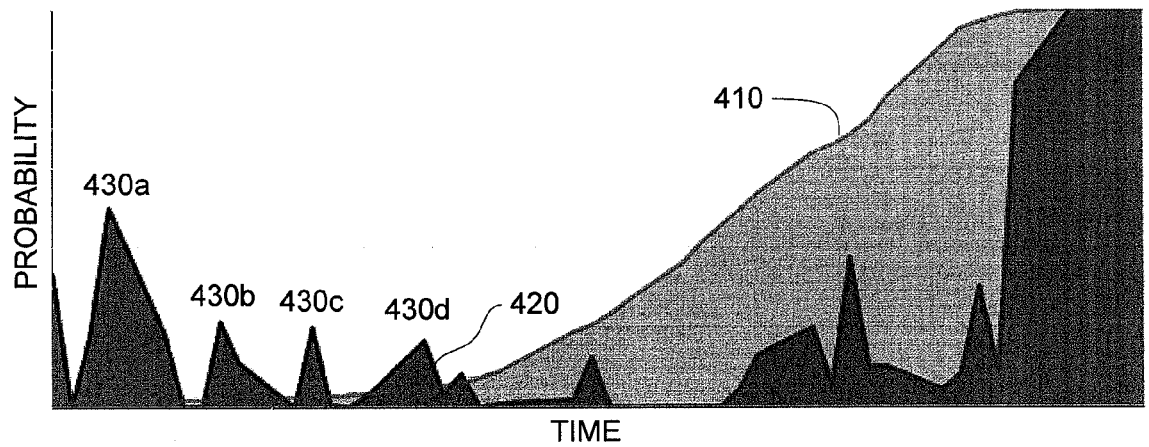
FIGS. 4A and 4B are diagrams illustrating exemplary outputs of the Naïve Bump Hunting process of FIG. 3.

Medical Group
Provider
Enrollment Category
Batch Format
Most Recent Claim Submission Date
Current Claim Status Using this information, cumulative probability distributions are calculated for each provider/payer combination, and bumps are identified in act 304 for each combination. FIG. 4A illustrates an example of how bumps are identified according to some embodiments of the invention. The graph in FIG. 4A illustrates the empirical survival distribution 410 and actual survival distribution 420 for one provider/payer combination. As described above, "bumps" are located at positions where the actual survival distribution 420 exceeds the estimated survival distribution 410. For example, in the graph of FIG. 4A, several bumps 430a-430d may be identified for further investigation.

After the bumps are identified, each bump is scored in act 306 to determine if the bump should be considered for further analysis. In some embodiments, a massless score Q(B), a mass score M(B), and a probability mass score Γ(B) are calculated for each Bump, B. according to the following formulas:

$$Q(B) = \sum_{t \in B} 1[\hat{p}_t > p_t](\hat{p}_t - p_t)$$

$$M(B) = \sum_{t \in B} 1[\hat{p}_t > p_t](\hat{p}_t - p_t)\alpha(c_t)$$

$$\Gamma(B) = \prod_{s \in B}^{t} \prod_{\lfloor (\hat{p}_t - p_t)c_s \rfloor} p(t-s)$$

where $\hat{p}_t$ and $p_t$ are the values from the actual and empirical cumulative distributions, respectively, and $\alpha(c_t)$ is a function of the claim volume. In some embodiments, Q(B) and M(B) are combined to generate an overall score, although in other embodiments, Γ(B) is compared to a threshold value to determine if the bump should be considered for further analysis in act 308. If the score is below the threshold value, the bump is categorized in act 310 using one or more scoring algorithms described in more detail below. However, if the score is above the threshold value, the bump is eliminated from further analysis in act 312. In act 314, it is determined if more bumps are to be categorized. If there are additional bumps to be categorized, the process returns to act 306 to compute the score for the next bump. When it has been determined that all of the bumps have been categorized, the underlying issue corresponding to the identified category for a bump is addressed in act 316 and the process ends.

Figure 4B:
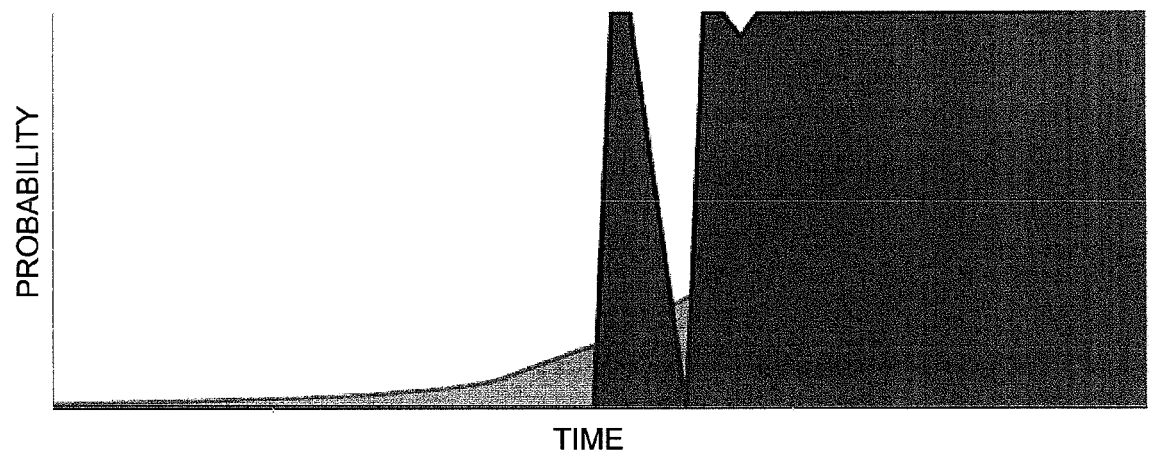

Categorizing the bumps will now be explained in more detail. In some embodiments of the invention, bumps are classified into one of at least four categories. Applicants have recognized that in some circumstances, when a new provider is added to a system with multiple providers and payers, remittance for initial claims submitted to a payer by the provider may not be received for some time. This behavior is captured by the category "Remittance Never Received." Bumps may be classified into this category if the bumps are contiguous in time, begin at the current date and show no remittance (i.e., have a no response probability value of 1). An example of this type of category is illustrated in FIG. 4B. As can be seen from the rightmost bump of FIG. 4B, remittance has never been received for this payer for this provider. It should be noted that the bump on the left is an artifact of the graph, and is part of the rightmost bump.

Applicants have also recognized that certain providers that have been receiving remittance for some time may suddenly stop receiving remittance from a particular payer. This behavior is captured by the category "Remittance Cessation." One possible reason why remittance cessation occurs is due to the provider signing up for Electronic Funds Transfer (EFT) without notifying the payer, although other circumstances may also result in remittance cessation. Bumps may be classified in the Remittance Cessation category if the bumps are contiguous from the current day, but there was remittance received by the provider in the past (unlike the Remittance Never Received category).

A third category is "Specific Remittance Failure" in which bumps are most commonly related to individual billing batches where 100% of the claims have not received remittance and are currently at the payer. In most of these cases, it is likely that the set of claims never made it into the payer's adjudication system. A fourth category is "General Remittance Failure." This category comprises all of the bumps that were not categorized into the other categories.

In some embodiments, clusters identified via cluster identification process 200 or cluster identification process 300 are scored to indicate how likely it is that the claims share a common root cause. Scoring the clusters facilitates the identification of clusters that have a high likelihood of having a shared root cause issue underlying the claims in the cluster. Thus, clusters with a high score are good candidates for further investigation into the root cause. In some embodiments, clusters with a high score may be given priority so that a follow-up communication with the payer is initiated early in the resolution process. One or more algorithms may be used to determine the score for a cluster, and not all algorithms may be used to score each type of cluster. In some implementations, if multiple algorithms are used to score a cluster, only the highest score is reported, although in other implementations, an average score may be used.

In some embodiments, automated information gathering may be used to facilitate the scoring process. For example, although some of the scoring algorithms described below make use of stored information to determine a score for a cluster, in some instances, additional information may be required to determine the validity of a cluster. In such cases, one or more requests may be automatically sent to users who may supply the additional information, and work on the cluster (e.g., scoring) may be temporarily suspended until the additional information is supplied. Thus, while a user is waiting for the additional information to be supplied, other clusters may be worked, thereby improving the efficiency by which clusters are processed.

Figure 5A:
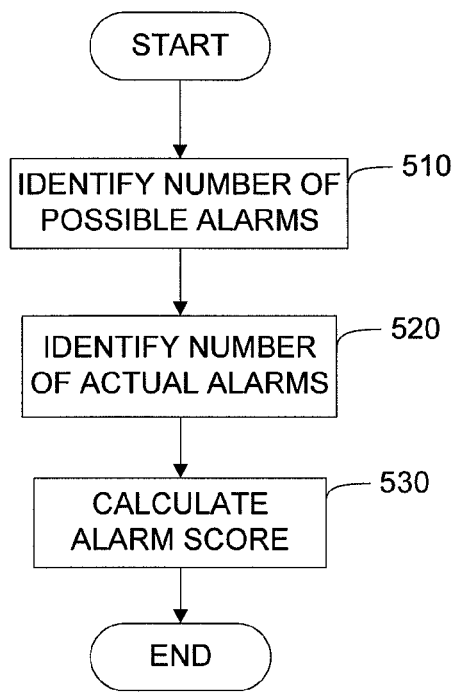
FIGS. 5A-5C are flow charts illustrating scoring strategies according to some embodiments of the invention.
Figure 5B:
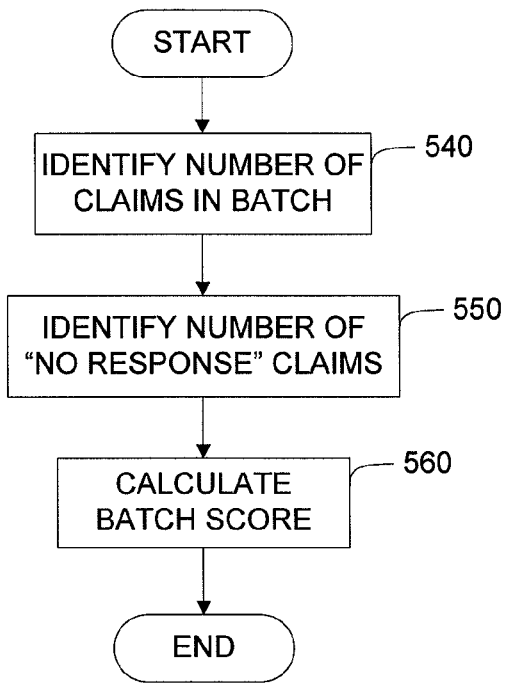
Figure 5C:
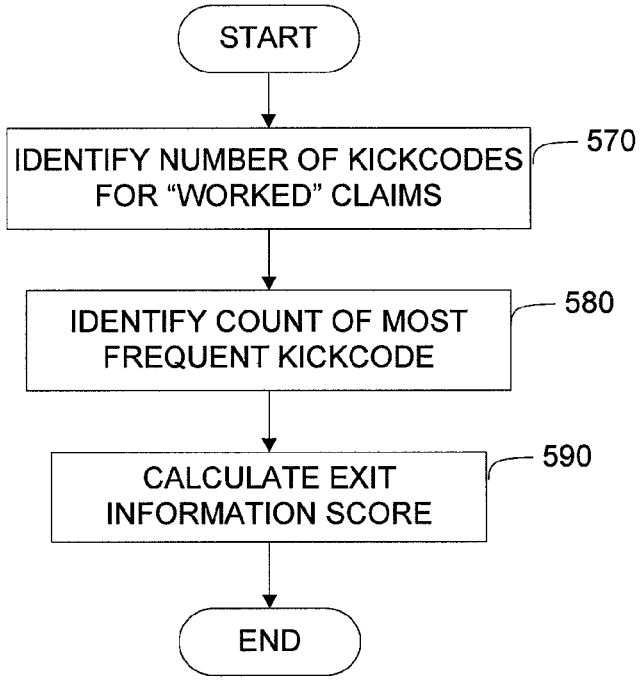

Flow charts for three exemplary scoring algorithms are illustrated in FIGS. 5A-5C. A first algorithm relates to claim alarm scoring. As described above, in some embodiments directed to claim tracking, when a claim is submitted to a payer, an alarm is set by specifying an alarm date by which a response should be received from the payer. If a response is not received by the alarm date the alarm is triggered and the status of the claim may be changed, for example, to Followup. An alarm may be deactivated if a response is received before the alarm date.

An alarm score is representative of the percentage of alarms that actually fired for a given cluster pattern. In act 510, the number of possible alarms for a particular cluster pattern is determined. In act 520, the actual number of alarms that were triggered is calculated, and in act 530, the alarm score is calculated by dividing the actual number of alarms by the number of possible alarms and multiplying by 100. For example, suppose in the past sixty days there were 100 claim alarms set to be triggered for a given Medical Group::IRC cluster pattern combination and 90 of these alarms were actually triggered. In this example, a cluster based on this Medical Group and IRC would have an alarm score of 90.

Another type of scoring algorithm relates to claims that are submitted in the same billing batch. Claims submitted in the same billing batch are submitted to the payer at the same time and via the same method. In all likelihood, if one of the claims is on file with the payer, then the other claims in the billing batch should also be on file with the payer.

A process for calculating a billing batch score is illustrated in FIG. 5B. In act 540 the number of claims in the billing batch is determined. In act 550 the number of claims that belonged to the billing batch and in which no response was received is determined. The billing batch score is calculated in act 560 by dividing the number of "no response" claims by the total number of claims in the billing batch and multiplying by 100. For example, if there were 100 claims in the billing batch and no payer response was received for 80 of the claims, the cluster would have a score of 80.

Another type of scoring algorithm is based on reviewing payer responses after the status of a claim was changed to Followup. Since clusters are comprised of claims whose status was changed to Followup within a certain time period (e.g., within the past 60 days), in some cases, a payer response will have been obtained after the status of the claim was changed to Followup. For example, remittance may be received by the provider shortly after an alarm date has passed or a follow-up communication with the payer may have resolved the problem.

When working a cluster, after the problem with a claim has been resolved, the reason why the status of a claim was changed may be recorded as a "kickcode." A process for calculating an exit information score by reviewing these post-Followup responses using information stored as kickcodes is illustrated in FIG. 5C. In act 570 the number of kickcodes for worked claims in a cluster is determined. In act 580, the count of most frequent kickcode is determined, and in act 590, the exit information score is calculated by dividing the count of the most frequent kickcode by the total number of kickcodes for worked claims and multiplying by 100. For example, suppose 100 claims have exited Followup status as the result of a payer response. In addition, suppose the most frequently used kickcode was CIP and it was employed 50 times. This would result in a score of 50 for the cluster.

In some embodiments, a quantity of claim alarms and/or kickcodes are compared to a threshold value and the corresponding alarm score/exit information score is only considered valid if the quantity of claim alarms/kickcodes exceeds the threshold value. Although three algorithms are described for scoring clusters, it should be appreciated that other types of scoring algorithms may also be employed and embodiments of the invention are not limited in this respect.

Figure 6:
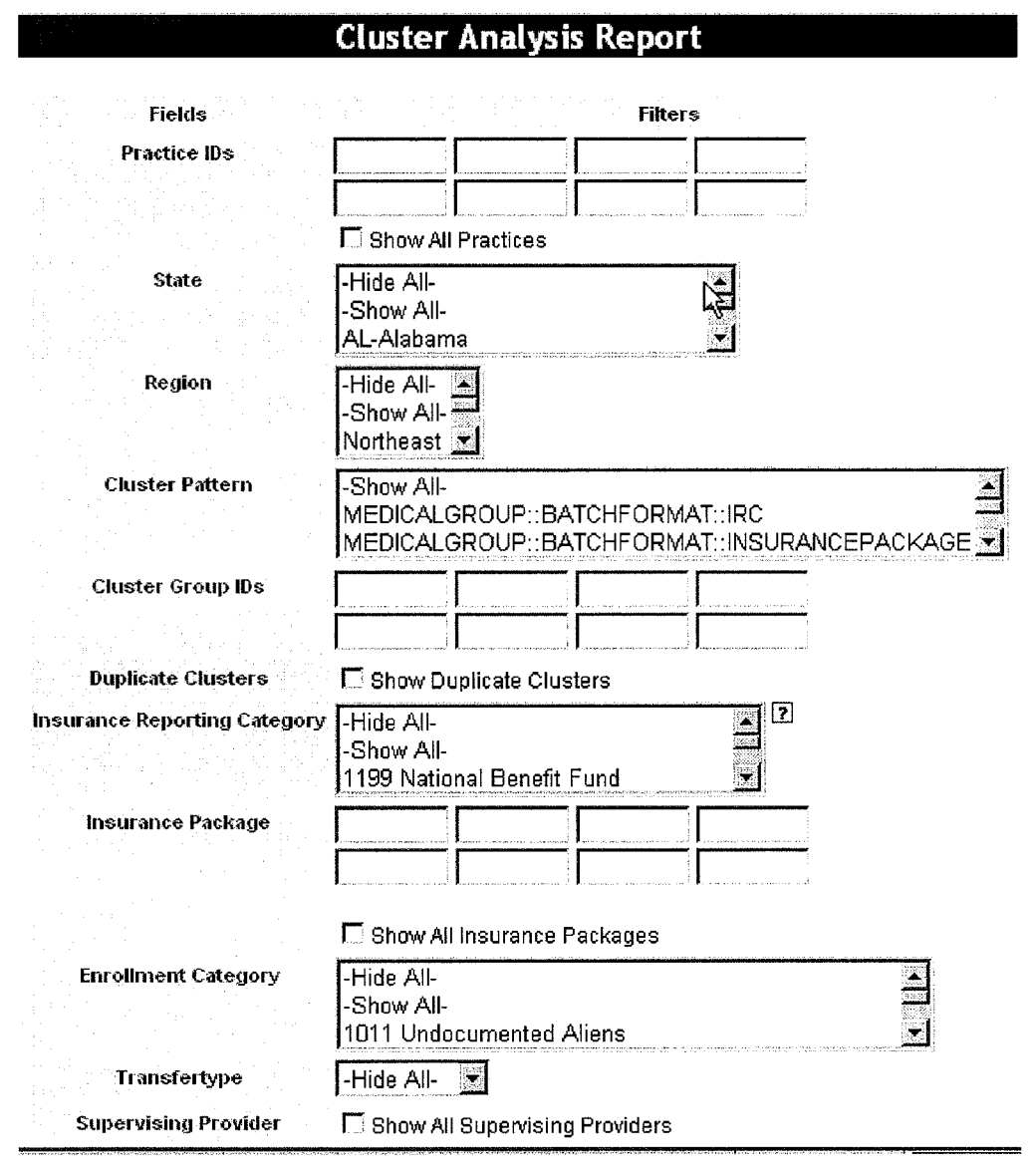

Once the clusters have been identified and scored, the results may be made available as a report to one or more users via a "Cluster Analysis Report" interface. The report allows users to generate a cross practice list of clusters which can then be "drilled into" so that their component claims can be reviewed. In addition to the score, the report comprises other information including: (1) The number of claims in Followup status, (2) The number of claims in Billed status, (3) The number of "worked" claims, and (4) The total claim count. An exemplary interface for a cluster analysis report generated by embodiments of the invention is illustrated in FIG. 6, and a corresponding report is illustrated in FIG. 7. The cluster analysis report interface in FIG. 6 comprises a plurality of fields that a user may interact with in order to select a cluster combination and other factors used to generate a report, such as the report in FIG. 7. The report may additionally comprise other information such as charts, tables, and graphs which enable a user to interact or "drill down" into the individual claims in a cluster to determine a root cause for the cluster.

As described above, Followup status refers to claims where an alarm has been triggered, indicating that the payer should be contacted and Billed status refers to claims where the alarm is set to be triggered in the near future (e.g., within the next five business days). By including both the Billed claims and the Followup claims in the cluster identification process, claims that have not yet triggered alarms may be dealt with proactively before an alarm is triggered.

An analysis process for "working" a cluster in accordance with some embodiments of the invention includes the following steps. First, a list of clusters may be reviewed for clusters with the best combination of "open" (Billed and Followup status) claims with a relatively high score. For example, in the exemplary report shown in FIG. 7, five clusters generated based on the cluster pattern "Billing Batch" are ranked according to their score. In short, clusters with the most claims and that have a significant likelihood that the claims share a common root cause are generally selected to be worked.

After a cluster has been selected to be worked, information is collected based on the specific cluster pattern which was used to generate the cluster. The information may be automatically collected from other parts of the integrated system or the information may be manually collected by a user, and embodiments of the invention are not limited in this respect. For example, if the cluster was generated based on the "Billing Batch" cluster pattern, then other claims from the same billing batch are reviewed to determine if responses have been received from the payer for those claims. The score of the cluster may be used to estimate the overall processing of the claims in a cluster. If a low number of responses is detected, the user may then review those individual claims to better understand their nature. The payer corresponding to the claims may then be contacted to verify the status of a few other claims in the billing batch.

Similarly, if the cluster was derived from the "Medical Group::Claim Submission Category" cluster pattern, then recent accounts receivable activity related to that pattern may be analyzed. Based on the initial analysis, the user may decide to contact the payer directly to confirm their analysis. For the previously mentioned "Medical Group::Claim Submission Category" cluster, if the user notices that there have been no recent payments, the payer may be contacted to verify the billing address of the medical group.

If it is determined that all claims in a cluster do not share a common root cause, the "Cluster Analysis Report" interface enables users to create subsets of the clusters. The subsets of clusters can then be analyzed in a similar manner as described above for the other clusters. For example, a user may investigate a cluster based on the medical group cluster pattern and after some analysis, determine that a root cause is shared between claims for a single provider in the medical group. A subcluster may be formed of just the claims for the single provider, and the user may then make a determination regarding whether the claims in the subcluster share a root cause. If it is determined that the claims in the subcluster do not share a root cause, the subcluster can be flagged as "Rejected," or alternatively, the subcluster may not be added to the database. However, if it is determined that the claims in the subcluster may share a root cause, the subcluster is added to the database and is "worked" as described above.

A next step in the cluster resolution process may be to remove claims from the queue after the common cause has been addressed. This may be accomplished by changing the status of the claim to a status that more accurately describes its condition with the payer. In addition, in some embodiments, a note may be appended to the claim which reflects cluster-related findings. For example, suppose it was determined that the claims belonging to a cluster were paid by the payer and that the checks were cashed by the provider. In this example, a duplicate explanation of benefits (BOB) may be requested from the payer, the status of the claims may be updated, and a note reflecting the research may be added.

As described above, one method for changing a claim's status is to add a "kickcode" to it. A kickcode provides a general description of why the claim was moved to a particular status. In the aforementioned example, the claim may be assigned a kickcode "TRAKREMIT" indicating that the check had been cashed by the provider more than thirty days ago. This would change the status of the claims to "Billed" since a response from the payer is expected—in this case, the duplicate BOB. A more cluster-specific note such as "Spoke to John Doe at the payer, the check was cashed on Jan. 1, 2009" may also be added.

Applicants have recognized that in systems in which clusters are worked by a plurality of users in a group, it may be advantageous to automatically assign particular clusters to be worked to particular users in the group. Thus, some embodiments of the invention are directed to automatically assigning a cluster to a user in a group after the cluster is generated according to one or more cluster identification processes. By assigning clusters to particular users, it may be easier to track which clusters are being worked and by whom. Such a system may also help ensure that high-volume clusters do not go unassigned, and that two users do not work duplicate work if they work on similar, but not "duplicate" clusters. It should be appreciated that some or all of the generated clusters may be automatically assigned to a user, whereas other clusters may be assigned manually.

An exemplary workflow for a cluster analysis process that can be used to work a cluster generated by the aforementioned cluster identification and generation processes according to some embodiments of the invention, is now described with reference to FIGS. 6-16. The cluster analysis process begins with a user interacting with a cluster analysis report interface as shown in FIG. 6. The user may interact with the interface to select various filtering options for generating a report of active clusters meeting specified criteria. For example, a user can filter based on certain cluster patterns or specific cluster IDs. Additionally, the user can also filter the results by including claims that meet certain characteristics (e.g., the IRC value is BCBC-MA). After selecting desired filtering options, a list of active clusters is generated as shown in FIG. 7. As described above, the list of active clusters includes information about the cluster pattern, score, and other information about the count and type of claims in each cluster.

Figure 8:
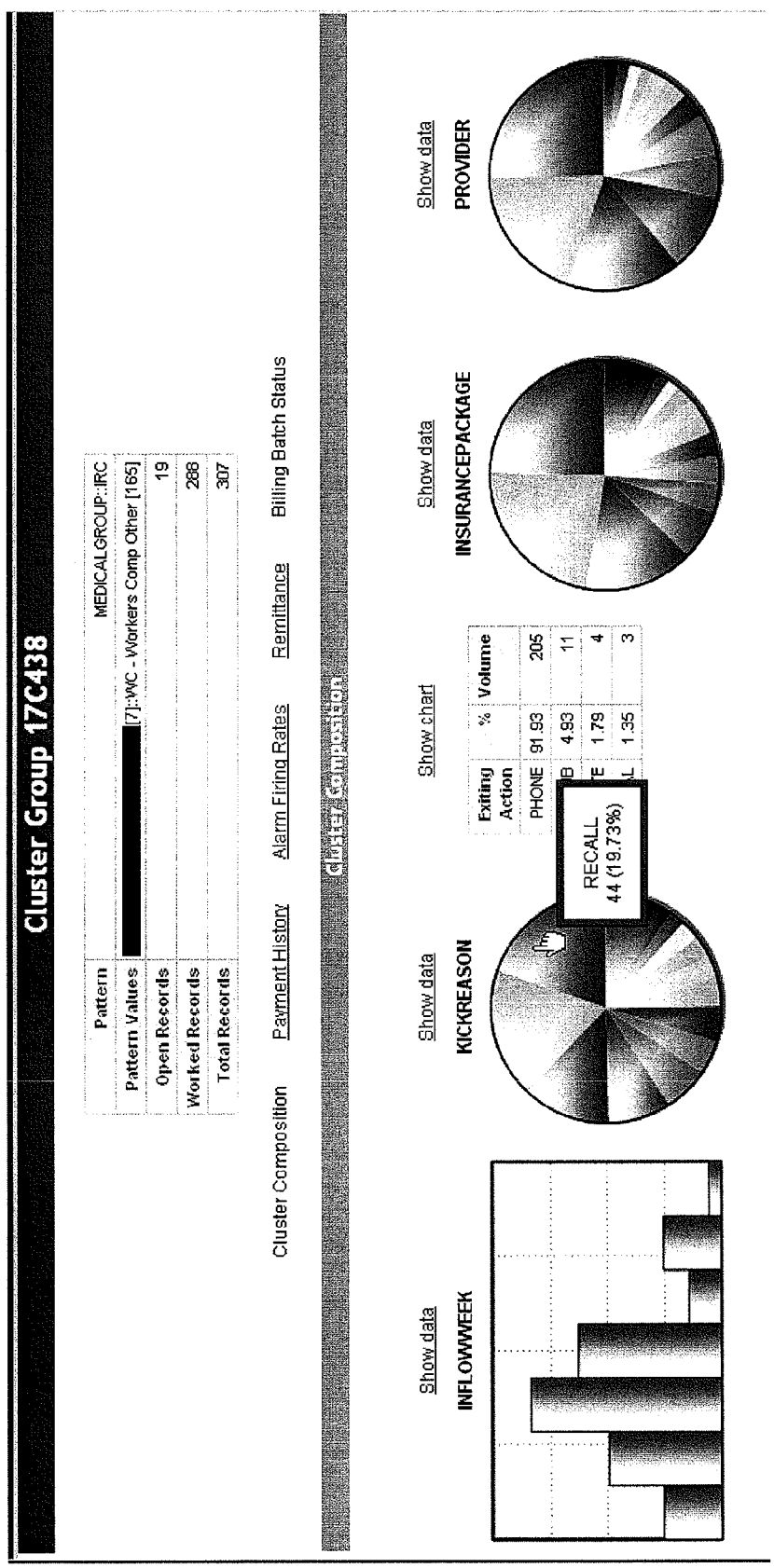
FIG. 8 is a display of a cluster composition report produced by a portion of a software program used to analyze clusters generated in accordance with some embodiments of the invention.
Figure 9:
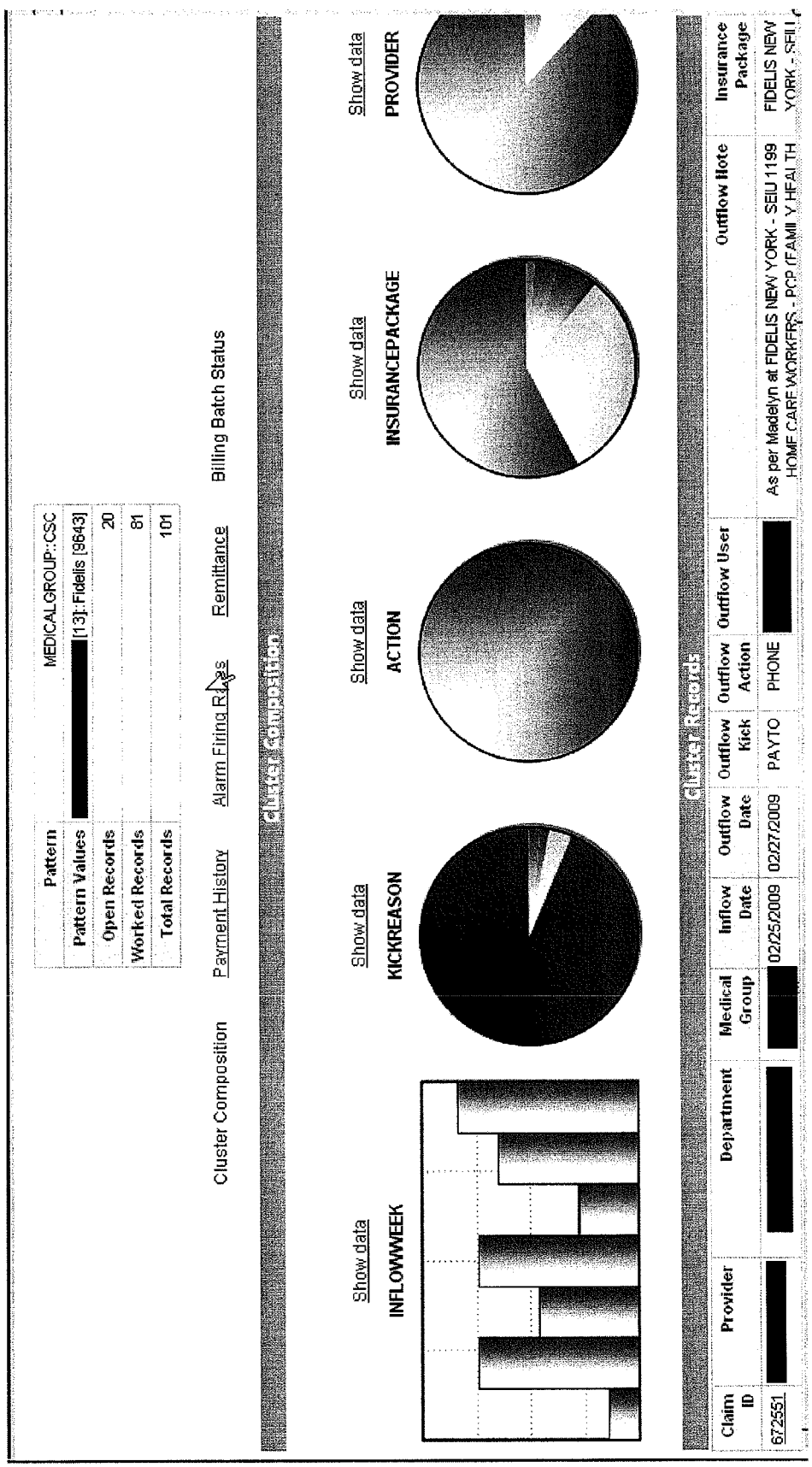
FIG. 9 is a display of a cluster record report produced by a portion of a software program used to analyze clusters generated in accordance with some embodiments of the invention.

The information listed in the report may be linked to additional information that may be helpful in enabling the user to determine a root cause for a cluster. For example, FIG. 8 shows another portion of a cluster group report which is used to provide additional details about the composition of a particular cluster that was selected from the report in FIG. 7. As can be seen from FIG. 8, a user may interact with various charts and graphs by placing a cursor over a portion of the graph or table to reveal the underlying data. If desired, a user may also examine information about claims in a cluster as shown in FIG. 9. When claims are selected, the claim ID and information about the claims including any actions taken or notes is displayed. This information may be useful to a user, among other things, to determine if multiple claims within the same cluster were handled in a similar manner. Although information for only a single claim is illustrated in FIG. 9, it should be appreciated that a report may display multiple claims.

A user may also learn about a cluster by viewing the individual claims that make up a cluster as shown in FIGS. 10 and 11. In FIG. 10, information about a cluster is displayed along with general information about the claims in the cluster. In FIG. 11, a more detailed view of all of the individual claims in the cluster is displayed. A user may use the information in the tables of FIGS. 10 and 11 to review notes made by other users who worked the claims. In addition, a user may decide to communicate with a payer regarding claims that have not yet received a response or will receive a response in the near future. By communicating with a payer, information may be collected and a hypothesis may be generated regarding a root cause for the claims in the cluster.

In some instances, a user may specify the "status" of a cluster. For example, a cluster may be marked as "Validated," "Rejected," or "Assigned," to indicate that the cluster has already been worked. By indicating the status of a cluster, users will be alerted to clusters that have already been analyzed and rejected so as not to spend more time reanalyzing such clusters, whereas clusters identified as "Validated" can be quickly processed by a user.

Figures 13A, 13B:
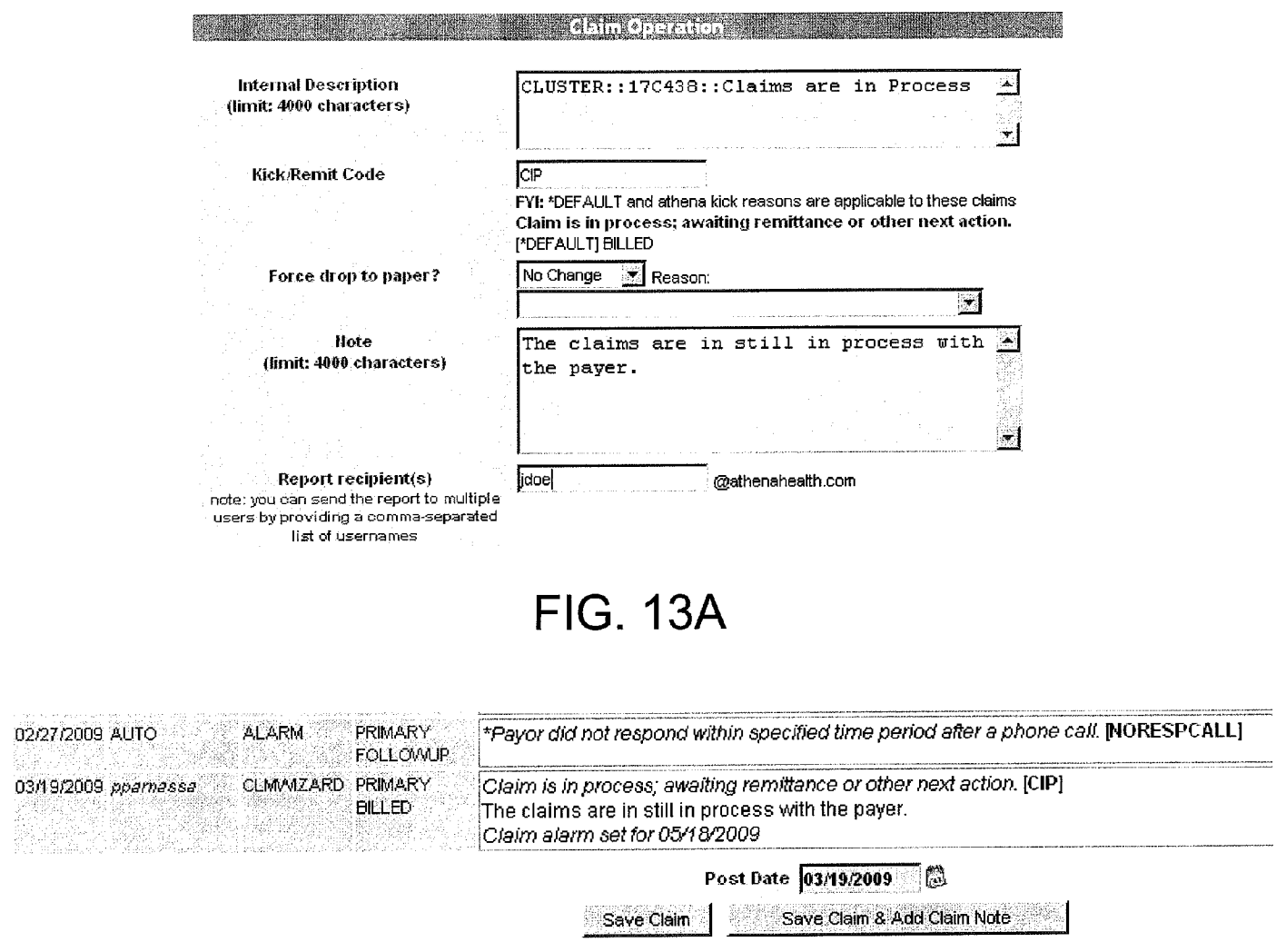

After a user has determined a root cause for the claims in the cluster, all of the claims in the cluster can be processed en masse as illustrated in FIG. 12. An analysis system for use with clusters generated according to embodiments of the invention may comprise a "Claim Processing Wizard" which is an interface that facilitates the processing of claims in a cluster. The claim processing wizard may list the claims and enable the user to specify the actions that should be taken on the claims. Exemplary actions that may be taken include the following: 1) "Kicking" the claims with a specified kickcode—this moves the claims to another status and specifies why they were moved to the new status, and 2) adding a brief note to the claim, explaining why the particular kickcode was used. An interface for entering a note is illustrated FIG. 13A, and an interface for editing information about a claim is illustrated in FIG. 13B.

In some implementations of the claim processing wizard, notes entered by a first user may be viewable to a second user in a group of users that is working clusters. For example, notes may be made available to users in the group as a portion of a software program executed on one or more computers connected via a network. By making notes accessible to one or more other users in a group of users, common root causes that are identified by one user may be easily shared with other users in the group resulting in increased productivity and improved reporting.

The collection of claims gathered by the claim processing wizard is referred to as a "claimset." The actions taken against claims in a claimset are taken en masse so that most or all of the claims belonging to a claimset are "kicked" at the same time. In some implementations, the claim processing wizard may accomplish this by adding a "claimnote" to each claim. For example, if claims are still in process with a payer, a claimnote with a "CIP" kickcode may be added to each claim in the claimset.

Depending on the nature of the cluster, claims outside of the cluster, but sharing similar characteristics may also be processed. This process, known as "Reach Into Billed," may be used when the problem identified by the cluster impacts all claims recently submitted to a payer. For example, if the ID number for a provider is incorrect, then all claims submitted to the payer will be lost (or denied). In this case, any claim recently billed to the payer will need to be resubmitted, not just those whose alarm has already been triggered.

An exemplary interface for a "Reach into Billed" process for analyzing clusters generated according to some embodiments of the invention is shown in FIG. 14. In "Reach into Billed," a user may select a time range and/or alarm date for claims to be searched for that are outside of a cluster but which share characteristics with claims in the cluster. A list of potential claims is returned in response to executing this process, and a user may select some or all of the claims in the list to be processed. In both the standard and "Reach into Billed" cluster process, claims are processed en masse via "claim sets" through the claim processing wizard. This claim set functionality allows a common note and kickcode to be applied to a defined set of claims.

Since clusters are likely to persist over time users may specify how future claims matching the specified cluster pattern should be processed. For example, suppose it is determined that the previously mentioned cluster A is a valid cluster and that all claims for it should be assigned the kickcode "TRAKREMIT." This information can be recorded and if additional claims enter Followup status that meet the conditions for belonging to cluster A, a user will know that (1) these new claims belong to a "validated" cluster group and (2) they should be assigned a kickcode of TRAKREMIT. In some embodiments, a cluster group may only remain valid for only a limited period of time. For example, if two claims both belong to the same cluster group but they entered Followup status one year apart, the reasons behind their movement into Followup status may be quite different.

Information about a cluster generated according to some embodiments of the invention may be stored using a "Cluster Group Admin" interface as illustrated in FIG. 15. The cluster group admin interface enables a user to record items such as the "recommended kickcode" for claims belonging to the cluster as well as the text of the associated claimnote. In some implementations of a cluster analysis system, the information from the cluster group admin interface may be automatically transferred throughout the cluster workflow process.

In some implementations of a cluster analysis process, a work report may be generated if the root cause determined for claims in a cluster may need to be handled by a particular user or department. For example, if a cluster has resulted from a bad "Pay-To" address, a report may be generated that can be forwarded to a user who deals with enrollment of payers and providers. Additionally, the group level information included in a work report may also be useful for a user working a cluster, as the group level information provides additional data that may be helpful in determining a root cause for the claims in the cluster. An example of a report generating interface for creating reports for clusters generated in accordance with embodiments of the invention is illustrated in FIG. 16.

Having thus described several aspects of some embodiments of this invention, it is to be appreciated that various alterations, modifications, and improvements will readily occur to those skilled in the art.

Such alterations, modifications, and improvements are intended to be part of this disclosure, and are intended to be within the spirit and scope of the invention. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The indefinite articles "a" and "an," as used herein, unless clearly indicated to the contrary, should be understood to mean "at least one."

The phrase "and/or," as used herein, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," shall have its ordinary meaning as used in the field of patent law.

As used herein in, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of processing a plurality of medical billing claims stored in a queue, wherein the medical billing claims stored in the queue are associated with a plurality of attributes identifying characteristics of the medical billing claims, the method comprising acts of:

grouping, by at least one computer processor, at least some of the plurality of medical billing claims into a first cluster based, at least in part, on a first cluster pattern indicating at least one shared attribute from among the plurality of attributes associated with the medical billing claims, wherein the medical billing claims in the first cluster are claims that have not received remittance from a payer or have been denied by a payer;

validating the first cluster using predetermined criteria to determine if the first cluster should be analyzed, discarded, and/or marked for further analysis;

collecting in response to determining that the first cluster should be analyzed, information about each of the medical billing claims in the first cluster, wherein the collected information relates to the at least one shared attribute of the first cluster pattern;

determining a root cause issue for the medical billing claims in the first cluster based on the collected information;

receiving a solution to the root cause issue for the medical billing claims in the first cluster;

storing information related to the solution to the root cause issue and the first cluster pattern and attributes to which the solution applies; and applying the solution to at least one new medical billing claim received after the information related to the solution has been stored.

2. The method of claim 1, further comprising:
grouping at least some of the plurality of medical billing claims stored in the queue into a second cluster based, at least in part, on the first cluster pattern;

assigning a first score to the first cluster indicating a first likelihood that the medical billing claims in the first cluster share a root cause issue;

assigning a second score to the second cluster indicating a second likelihood that the medical billing claims in the second cluster share a root cause issue; and collecting for each of the medical billing claims in the second cluster, information relating to the at least one shared attribute of the first cluster pattern;

wherein an order for performing the acts of collecting information about each of the medical billing claims in the first cluster and collecting information about each of the medical billing claims in the second cluster is determined based on a comparison of the first score assigned to the first cluster and the second score assigned to the second cluster.

3. The method of claim 1, wherein the first cluster comprises medical billing claims for which remittance was not received from a payer.

4. The method of claim 1, wherein the first cluster comprises medical billing claims which were denied by a payer.

5. The method of claim 1, wherein validating comprises:
determining a number of medical billing claims in the first cluster; and
determining that the first cluster should be analyzed when the number of medical billing claims in the first cluster is greater than a threshold value.

6. The method of claim 1, wherein validating comprises:
determining that the first cluster should be discarded if at least one value for the at least one shared attribute for the first cluster pattern is too general to result from a single root cause issue.

7. The method of claim 1, wherein validating comprises:
determining that the first cluster should be marked for further analysis if another cluster exists that comprises a shared number of medical billing claims that is greater than a threshold value.

8. The method of claim 1, wherein collecting information comprises accessing a table in a relational database that stores the information.

9. The method of claim 1, further comprising:
updating a status of each of the medical billing claims in the first cluster in response to receiving the solution.

10. The method of claim 1, wherein determining a root cause issue for the plurality of medical billing claims in the first cluster based on the collected information comprises interacting with a graphical user interface that provides directed guidance for determining the root cause issue.

11. A non-transitory computer-readable medium encoded with a plurality of instructions, that when executed by a computer, perform a method of processing a plurality of medical billing, wherein the medical billing claims stored in the queue are associated with a plurality of attributes identifying characteristics of the medical billing claims, the method comprising acts of:

grouping, at least some of the plurality of medical billing claims into a first cluster based, at least in part, on a first cluster pattern indicating at least one shared attribute from among the plurality of attributes associated with the medical billing claims, wherein the medical billing claims in the first cluster are claims that have not received remittance from a payer or have been denied by a payer;

validating the first cluster using predetermined criteria to determine if the first cluster should be analyzed, discarded, and/or marked for further analysis;

collecting in response to determining that the first cluster should be analyzed, information about each of the medical billing claims in the first cluster, wherein the collected information relates to the at least one shared attribute of the first cluster pattern;

determining a root cause issue for the medical billing claims in the first cluster based on the collected information;

receiving a solution to the root cause issue for the medical billing claims in the first cluster;

storing information related to the solution to the root cause issue and the first cluster pattern and attributes to which the solution applies; and applying the solution to at least one new medical billing claim received after the information related to the solution has been stored.

12. The computer readable medium of claim 11, wherein the method further comprises:
grouping at least some of the plurality of medical billing claims stored in the queue into a second cluster based, at least in part, on the first cluster pattern;

assigning a first score to the first cluster indicating a first likelihood that the medical billing claims in the first cluster share a root cause issue;

assigning a second score to the second cluster indicating a second likelihood that the medical billing claims in the second cluster share a root cause issue; and collecting for each of the medical billing claims in the second cluster, information relating to the at least one shared attribute of the first cluster pattern;

wherein an order for performing the acts of collecting information about each of the medical billing claims in the first cluster and collecting information about each of the medical billing claims in the second cluster is determined based on a comparison of the first score assigned to the first cluster and the second score assigned to the second cluster.

13. The computer readable medium of claim 11, wherein the first cluster comprises medical billing claims for which remittance was not received from a payer.

14. The computer readable medium of claim 11, wherein the first cluster comprises medical billing claims which were denied by a payer.

15. The computer readable medium of claim 11, wherein validating comprises:
- determining a number of medical billing claims in the first cluster; and
- determining that the first cluster should be analyzed when the number of medical billing claims in the first cluster is greater than a threshold value.

16. The computer readable medium of claim 11, wherein validating comprises:
- determining that the first cluster should be discarded if at least one value for the at least one shared attribute for the first cluster pattern is too general to result from a single root cause issue.

17. The computer readable medium of claim 11, wherein validating comprises:
- determining that the first cluster should be marked for further analysis if another cluster exists that comprises a shared number of medical billing claims that is greater than a threshold value.

18. The computer readable medium of claim 11, wherein collecting information comprises accessing a table in a relational database that stores the information.

19. The computer readable medium of claim 11, wherein the method further comprises:
- updating a status of each of the medical billing claims in the first cluster in response to receiving the solution.

20. The computer readable medium of claim 11, wherein determining a root cause issue for the plurality of medical billing claims in the first cluster based on the collected information comprises interacting with a graphical user interface that provides directed guidance for determining the root cause issue.

21. A medical billing claim processing system comprising:
at least one processor configured to:
- group a plurality of medical billing claims into a first cluster based, at least in part, a first cluster pattern indicating at least one shared attribute from among a plurality of attributes associated with the medical billing claims, wherein the medical billing claims in the first cluster are claims that have not received remittance from a payer or have been denied by a payer;
- validate the first cluster using predetermined criteria to determine if the first cluster should be analyzed, discarded, and/or marked for further analysis;
- collect in response to determining that the first cluster should be analyzed, information about each of the medical billing claims in the first cluster, wherein the collected information relates to the at least one shared attribute of the first cluster pattern;
- determine a root cause issue for the medical billing claims in the first cluster based on the collected information;
- receive a solution to the root cause issue for the medical billing claims in the first cluster;
- store information related to the solution to the root cause issue and the first cluster pattern and attributes to which the solution applies; and
- apply the solution to at least one new medical billing claim received after the information related to the solution has been stored.

22. The system of claim 21, wherein the at least one processor is further configured to:
- group at least some of the plurality of medical billing claims into a second cluster based, at least in part, on the first cluster pattern;
- assign a first score to the first cluster indicating a first likelihood that the medical billing claims in the first cluster share a root cause issue;
- assign a second score to the second cluster indicating a second likelihood that the medical billing claims in the second cluster share a root cause issue; and
- collect for each of the medical billing claims in the second cluster, information relating to the at least one shared attribute of the first cluster pattern;
- wherein an order for performing the acts of collecting information about each of the medical billing claims in the first cluster and collecting information about each of the medical billing claims in the second cluster is determined based on a comparison of the first score assigned to the first cluster and the second score assigned to the second cluster.

23. The system of claim 21, wherein the first cluster comprises medical billing claims for which remittance was not received from a payer.

24. The system of claim 21, wherein the first cluster comprises medical billing claims which were denied by a payer.

25. The system of claim 21, wherein validating the first cluster comprises:
- determining a number of medical billing claims in the first cluster; and
- determining that the first cluster should be analyzed when the number of medical billing claims in the first cluster is greater than a threshold value.

26. The system of claim 21, wherein validating the first cluster comprises determining that the first cluster should be discarded if at least one value for the at least one shared attribute for the first cluster pattern is too general to result from a single root cause issue.

27. The system of claim 21, wherein validating the first cluster comprises determining that first cluster should be marked for further analysis if another cluster exists that comprises a shared number of medical billing claims that is greater than a threshold value.

28. The system of claim 21, wherein collecting information comprises collecting information by accessing a table in a relational database that stores the information.

29. The system of claim 21, wherein the at least one processor is further configured to:
- update a status of each of the medical billing claims in the first cluster in response to receiving the solution.

30. The system of claim 21, wherein the at least one processor is further configured to:
- provide a graphical user interface with which a user may interact to receive directed guidance to determine the root cause issue.

* * * * *